US011771813B2

(12) United States Patent
Zambianchi et al.

(10) Patent No.: US 11,771,813 B2
(45) Date of Patent: *Oct. 3, 2023

(54) HYDROPHOBIC FILTER FOR FILTERING AN AIRFLOW OR ANOTHER GASEOUS FLOW IN A MEDICAL APPLICATION

(71) Applicant: Fresenius HemoCare Italia S.r.l., Mirandola (IT)

(72) Inventors: Laura Zambianchi, Reggio Emilia (IT); Paolo Verri, Carpi (IT); Paolo Radighieri, Concordia Sulla Secchia (IT); Giuseppe Mulas, Modena (IT)

(73) Assignee: Fresenius HemoCare Italia S.r.l., Mirandola (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/569,580

(22) Filed: Jan. 6, 2022

(65) Prior Publication Data
US 2022/0126011 A1  Apr. 28, 2022

Related U.S. Application Data

(63) Continuation of application No. 16/346,604, filed as application No. PCT/EP2018/052532 on Feb. 1, 2018, now Pat. No. 11,260,158.

(30) Foreign Application Priority Data

Feb. 28, 2017 (EP) .................................... 17425020

(51) Int. Cl.
*B01D 46/00* (2022.01)
*B01D 46/10* (2006.01)
*A61M 1/36* (2006.01)

(52) U.S. Cl.
CPC ........ *A61M 1/3638* (2014.02); *A61M 1/3627* (2013.01); *A61M 1/3667* (2014.02);
(Continued)

(58) Field of Classification Search
CPC ................ B01D 46/0005; B01D 46/10; B01D 46/0012; A61M 1/3627; A61M 1/3628; A61M 1/3668; A61M 1/00; A61M 5/165
(Continued)

(56) References Cited

U.S. PATENT DOCUMENTS

| 4,657,570 A | 4/1987 | Gronholz et al. |
| 4,806,135 A | 2/1989 | Siposs |

(Continued)

FOREIGN PATENT DOCUMENTS

| CN | 102580448 A | 7/2012 |
| CN | 102600669 A | 7/2012 |

(Continued)

OTHER PUBLICATIONS

Extended European Search Report, dated Dec. 14, 2022, for application No. EP22198105.3-1101.
(Continued)

*Primary Examiner* — Minh Chau T Pham
(74) *Attorney, Agent, or Firm* — Cook Alex Ltd.

(57) ABSTRACT

A hydrophobic filter for filtering an airflow or another gaseous flow in a medical application has a housing encompassing a filter chamber, an inlet port arranged on the housing and forming an inlet opening, an outlet port arranged on the housing and forming an outlet opening, and a hydrophobic structure extending along a plane of extension and separating the filter chamber into an inlet chamber and an outlet chamber. The inlet opening opens into the inlet chamber and the outlet opening opens into the outlet chamber. Herein, the outlet opening opens into the outlet chamber at a first location when viewed along the plane of extension and the inlet opening opens into the inlet chamber at a second location different from the first location when viewed along the plane of extension.

20 Claims, 7 Drawing Sheets

(52) U.S. Cl.
CPC ......... *B01D 46/0005* (2013.01); *B01D 46/10* (2013.01); *B01D 46/0012* (2013.01)

(58) Field of Classification Search
USPC ... 55/385.1, 385.4, 485, 486, 522, 524, 527; 428/246, 284; 604/23–28, 30–35, 41, 45, 604/164.01
See application file for complete search history.

(56) References Cited

U.S. PATENT DOCUMENTS

| | | | |
|---|---|---|---|
| 5,230,727 A | | 7/1993 | Pound et al. |
| 8,608,816 B2* | | 12/2013 | Palmerton ............... A61M 1/60 |
| | | | 604/35 |
| 9,415,160 B2* | | 8/2016 | Bonano .................... A61M 1/60 |
| 9,867,914 B2* | | 1/2018 | Bonano .................. A61M 5/165 |
| 10,898,622 B2* | | 1/2021 | Shelton, IV ....... B01D 46/0086 |
| 11,260,158 B2* | | 3/2022 | Zambianchi ........ A61M 1/3638 |
| 2007/0110612 A1* | | 5/2007 | Ito ....................... A61M 1/3638 |
| | | | 604/6.11 |
| 2009/0301475 A1 | | 12/2009 | Korneff |

FOREIGN PATENT DOCUMENTS

| | | |
|---|---|---|
| CN | 204034521 U | 12/2014 |
| CN | 103503815 B | 5/2015 |
| DE | 20 2015 104 135 U1 | 10/2015 |
| JP | 2011183331 A | 9/2011 |
| TW | 436314 B | 5/2001 |

OTHER PUBLICATIONS

International Search Report And The Written Opinion Of The international Searching Authority for PCT Patent Application No. PCT/EP2018/052532, dated May 15, 2018.

* cited by examiner

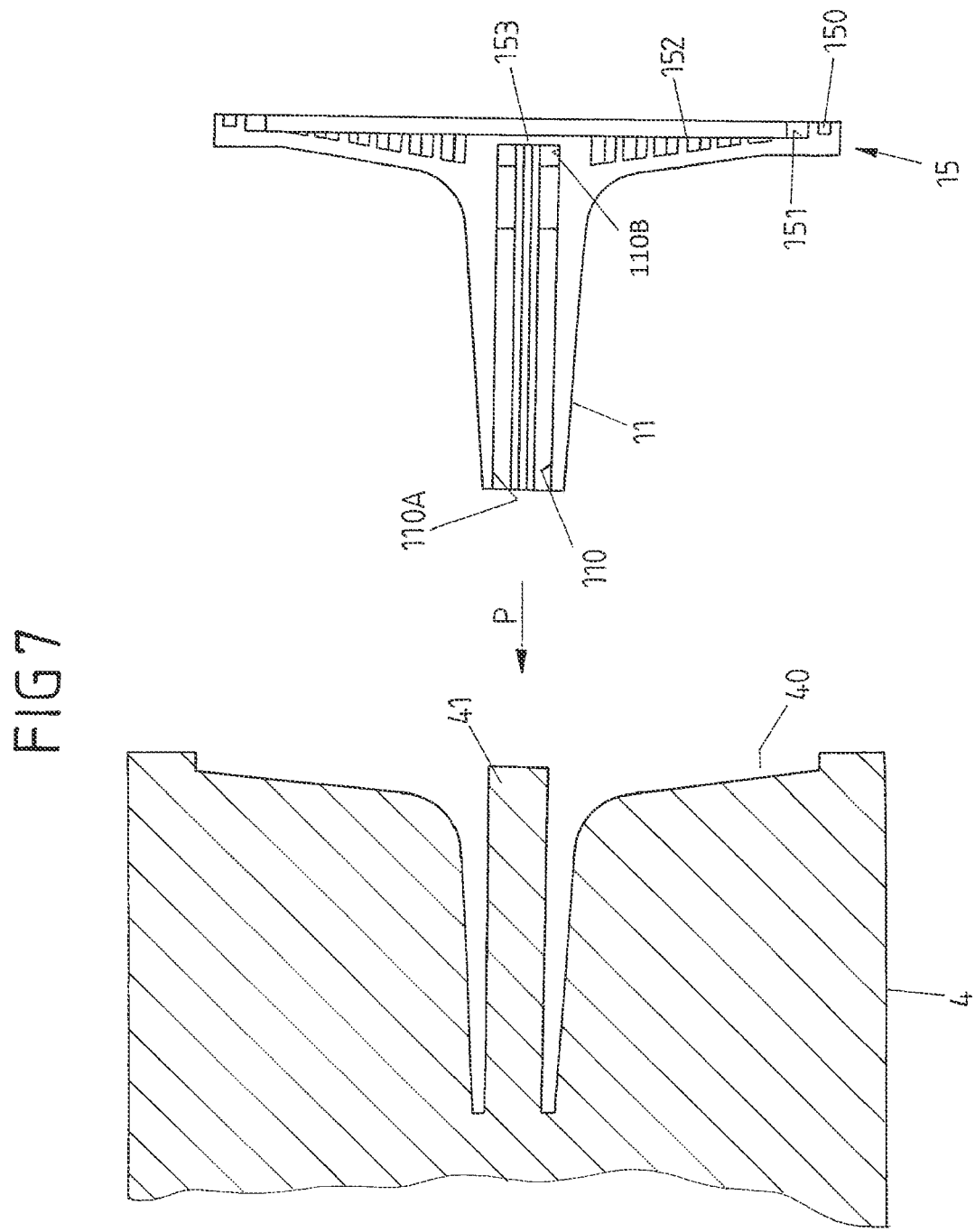

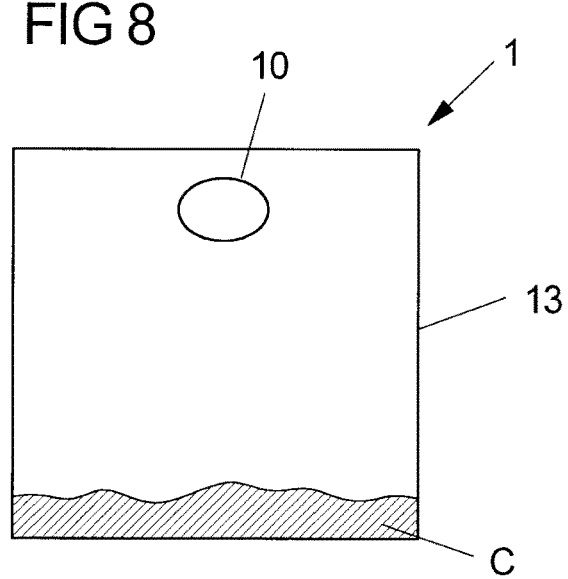
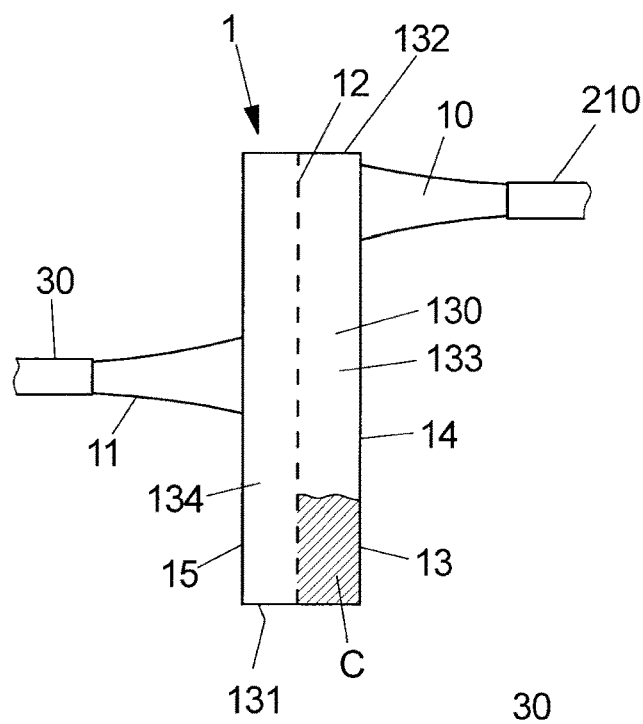
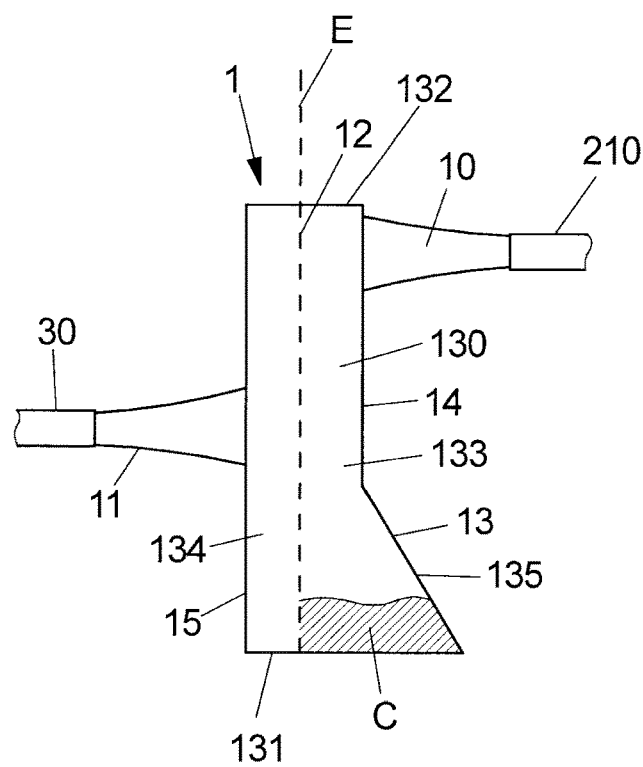

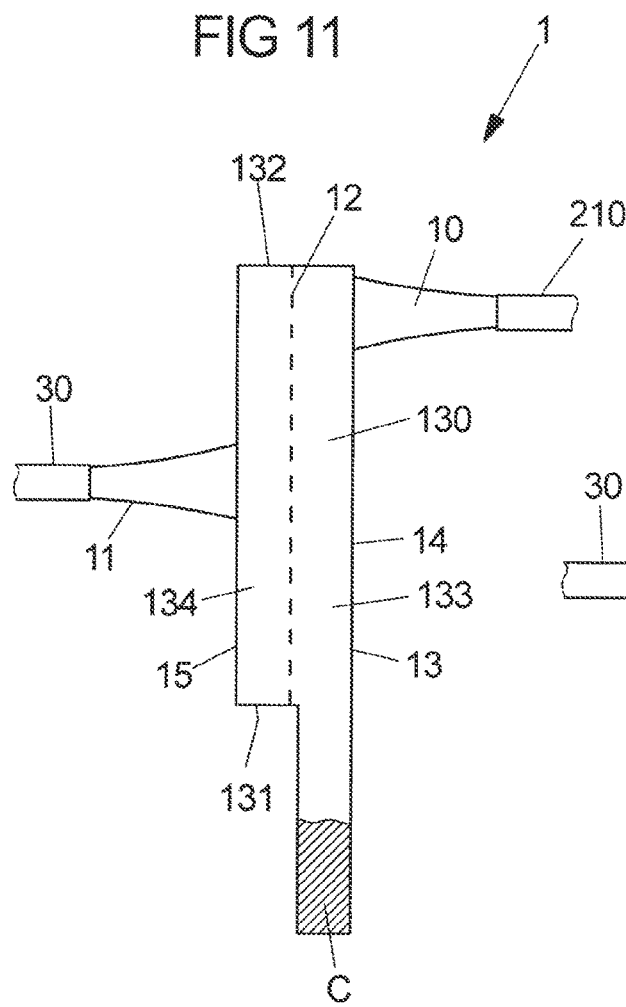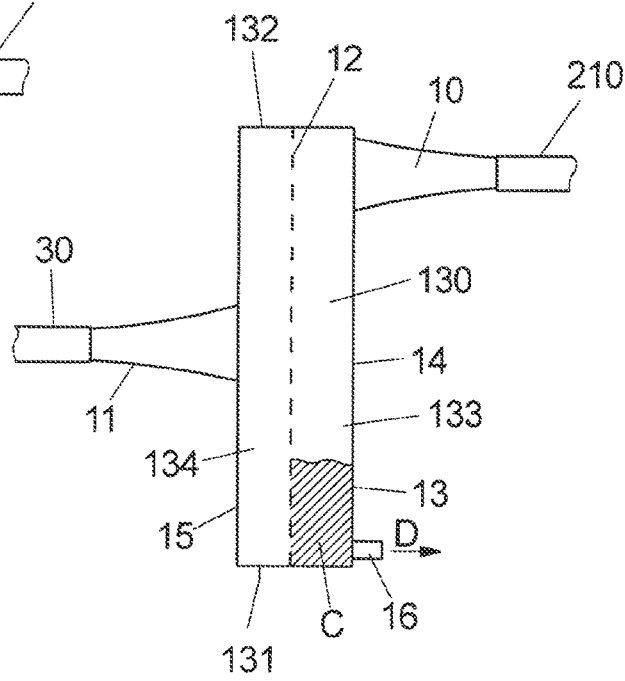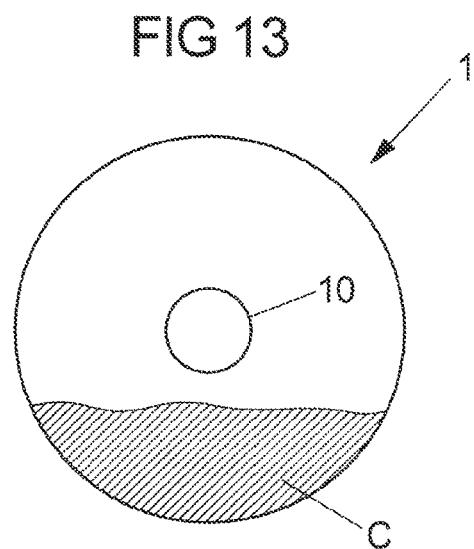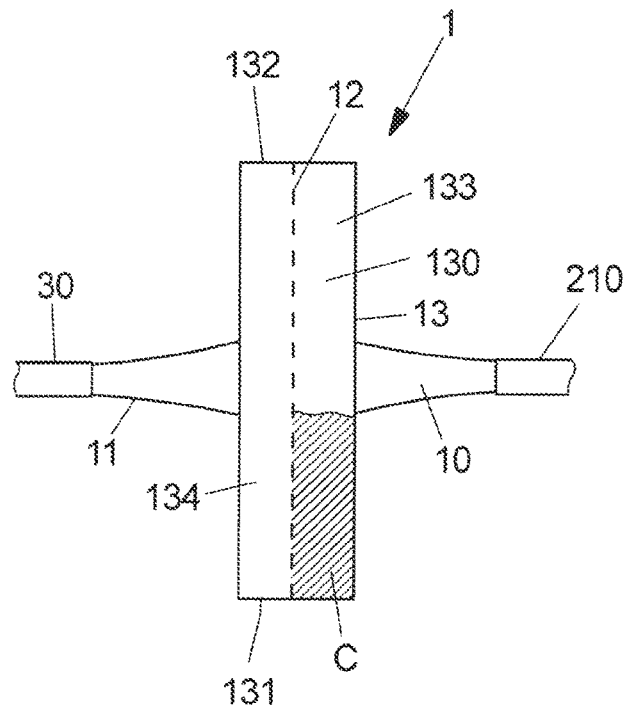

HYDROPHOBIC FILTER FOR FILTERING AN AIRFLOW OR ANOTHER GASEOUS FLOW IN A MEDICAL APPLICATION

RELATED APPLICATIONS

This application is a continuation of U.S. patent application Ser. No. 16/346,604, filed May 1, 2019, now U.S. Pat. No. 11,260,158 B2, which is a U.S. national stage application of PCT Patent Application Serial No. PCT/EP2018/052532, filed Feb. 1, 2018, which claims priority to European Patent Application Serial No. 17425020.9, filed Feb. 28, 2017, the contents of which are hereby incorporated by reference herein.

The invention relates to a hydrophobic filter for filtering an airflow or another gaseous flow in a medical application according to the preamble of claim 1.

A hydrophobic filter of this kind comprises a housing encompassing a filter chamber, an inlet port arranged on the housing and forming an inlet opening, an outlet port arranged on the housing and forming an outlet opening, and a porous filtering media comprising a hydrophobic structure, e.g. a hydrophobic membrane, extending along a plane of extension and separating the filter chamber into an inlet chamber and an outlet chamber, wherein the inlet opening opens into the inlet chamber and the outlet opening opens into the outlet chamber.

A hydrophobic filter of this kind may for example be used in connection with an autotransfusion system. Herein, using a negative-pressure pump, for example a vacuum pump, blood may be collected in a reservoir by creating a negative pressure in the reservoir by means of the pump and by sucking blood from a surgical site of a patient into the reservoir. The hydrophobic filter herein is used on the negative-pressure line connecting the reservoir to the pump to filter an airflow streaming towards the pump in order to avoid liquid and debris to be transported towards the pump and to prevent a damaging of the pump.

During operation, air is drawn through the filter, the air entering into the filter chamber through the inlet port, passing through the hydrophobic structure, e.g. in the shape of a membrane, and exiting from the filter chamber through the outlet port towards the pump. The hydrophobic structure is designed to let air or other gases pass, but to prevent water or other aqueous solutions from passing through the structure. Hence, the airflow is filtered such that no liquid or debris may enter the pump.

During a surgery, an autotransfusion system may be used continuously over multiple hours. During prolonged operation, condensation may occur in the hydrophobic filter, leading to condensation liquid (and other liquids or particles, subsequently in short referred to as condensation liquid) collecting in the inlet chamber of the filter. If such condensation liquid fills the inlet chamber to a substantial extent, the condensation liquid may hinder air from passing through the filter and may act like a plug preventing a further use of the filter. If this occurs during a surgery, it may be required to exchange the filter, which is to be avoided.

It is an object of the instant invention to provide a hydrophobic filter which remains usable despite a potential occurrence of condensation liquid in the inlet chamber.

This object is achieved by means of the filter comprising the features of claim 1.

Accordingly, the outlet opening opens into the outlet chamber at a first location when viewed along the plane of extension and the inlet opening opens into the filter chamber at a second location different from the first location when viewed along the plane of extension.

In particular, the housing may comprise a bottom and a top, wherein the second location is displaced with respect to the first location towards the top.

When used for example on an autotransfusion system, the filter is for example connected to the system in a defined position, the bottom of the housing of the filter being arranged at a lower location than the top. Because the inlet opening opens into the inlet chamber at the second location being displaced with respect to the first location towards the top, condensation liquid may collect in the inlet chamber beneath the inlet opening, such that condensation liquid does not block air from flowing through the inlet port into the inlet chamber and through the filtering media comprising the hydrophobic structure into the outlet chamber, the filter hence remaining functional despite the collection of condensation liquid in the inlet chamber.

The first location may, in one embodiment, be aligned with a location at which an axis of symmetry traverses the plane of extension of the hydrophobic structure. The second location is displaced with respect to the first location when viewed along the plane of extension, in particular towards the top.

By having the inlet opening entering into the inlet chamber at a location (when viewed along the plane of extension of the hydrophobic structure) different than the location at which the outlet opening opens into the outlet chamber, the filter may be designed such that a substantial amount of condensation liquid may be collected in the inlet chamber before a blockage of the filtration operation occurs. In particular, the inlet chamber may be designed such that the available volume in the inlet chamber for collecting condensation liquid is sufficient for receiving condensation liquid in an amount which reasonably can be expected over a prolonged duration of a surgery.

In another aspect, the inlet chamber may be designed to form a collection chamber which is suited to collect a substantial amount of condensation liquid in the region of the bottom of the housing.

In a first embodiment, the inlet chamber may comprise a tapering structure being tapered in a direction pointing away from the hydrophobic structure, the tapering structure forming the collection chamber. The tapering structure may for example have a pyramid shape or a conical shape (the conical axis being directed perpendicular to the plane of extension of the hydrophobic structure), such that the inlet chamber comprises a volume large enough to collect a substantial amount of condensation liquid. The tapering structure serves to increase the volume of the inlet chamber, such that condensation liquid may be collected at the bottom of the inlet chamber without blocking a substantial area of the hydrophobic structure and hence without substantially impacting the filtration performance of the hydrophobic filter.

In one embodiment, the inlet chamber may comprise an inlet structure adjoining the tapering structure at a side facing away from the hydrophobic structure. The inlet port herein is for example formed on the inlet structure and opens into the inlet chamber at a location substantially removed (along a direction perpendicular to the plane of extension) from the hydrophobic structure, wherein the inlet structure may be shaped such that air may beneficially flow into the inlet chamber to efficiently pass through the hydrophobic structure, e.g. the membrane, towards the outlet port.

In one embodiment, the inlet structure may comprise a curved guide face formed to guide air into the inlet chamber.

A planar face extends at an angle, for example 90°, with respect to the guide face, the inlet port being arranged on the planar face. Air entering into the inlet chamber through the inlet port hence impinges on the guide face and is guided by the guide face towards the hydrophobic structure such that a beneficial flow towards the hydrophobic structure is caused.

In another embodiment, the inlet chamber may widen towards the bottom to form the collection chamber in the vicinity of the bottom. For example, when viewed in a vertical cross-section (from bottom to top) perpendicular to the plane of extension of the hydrophobic structure, the inlet chamber may have a polygonal shape, the back wall of the housing (opposite to the structure) being tapered towards the top such that the inlet chamber at the bottom of the housing is substantially wider than at the top of the housing. In this way, a substantial volume at the bottom of the housing is created on the side of the inlet chamber, such volume being suited to collect a substantial amount of condensation liquid.

In another embodiment, the collection chamber may be formed on the side of the inlet chamber such that it extends beneath a bottom edge of the hydrophobic structure. The condensation liquid hence may be collected in the collection chamber beneath the hydrophobic structure such that the condensation liquid does not block a substantial area of the hydrophobic structure during operation of the filter and hence does not have an effect on the filtration performance.

In another aspect, a drainage port may be provided on the inlet chamber. The drainage port may in particular be formed in the region of the bottom of the housing such that condensation liquid may be drawn from the inlet chamber. By draining condensation liquid from the inlet chamber, filtration performance can be maintained in that condensation liquid can be removed from the inlet chamber as soon as a substantial amount of condensation liquid has collected in the inlet chamber.

In another aspect, the outlet opening may extend, in the shape of a channel, along a horizontal direction directed perpendicular to the plane of extension for guiding the airflow or another gaseous flow out of the filter chamber along the horizontal direction. Air hence exits from the filter chamber along the horizontal direction directed perpendicular to the plane of extension, hence along the direction in which the air passes through the hydrophobic structure, e.g. in the shape of a membrane. Herein it may be provided that the inlet opening extends, in the form of a channel, along a vertical direction directed parallel to the plane of extension and hence directed transverse to the horizontal direction. Air hence is guided into the inlet chamber along a direction different from the horizontal direction. This may on the one hand be beneficial to guide air into the inlet chamber of the filter such that liquid and particles carried with the air collect at the bottom of the inlet chamber. This may also be beneficial to be able to suitably lay a line in between a reservoir and the filter for collecting blood in the context of an autotransfusion system.

The housing may for example be formed by two separate housing members which are connected to each other for example by welding and which hold the hydrophobic structure in between themselves. The inlet port may for example be arranged on a first housing member, wherein the outlet port is arranged on a second housing member. The hydrophobic structure, e.g. in the shape of a membrane, may be clamped in between a first clamping section of the first housing member and a second clamping section of the second housing member such that the structure is held in between the housing members by clamping. The clamping section of the first housing member respectively the second housing member extends circumferentially along a circumferential edge of the first housing member respectively the second housing member such that the hydrophobic structure is held along its circumference in between the housing members.

In addition to the clamping, the hydrophobic structure may be welded to the first housing member and/or the second housing member.

In another aspect, the first housing member may comprise a first support structure formed by a multiplicity of ridges. The ridges may for example extend transverse to the plane of extension of the hydrophobic structure and may protrude from a back wall of the first housing member towards the hydrophobic structure.

Likewise, the second housing member may comprise a second support structure formed by a multiplicity of ridges, the ridges extending for example transverse to the plane of extension of the hydrophobic structure and protruding from a back wall of the second housing member towards the hydrophobic structure.

Each support structure is suited to support the hydrophobic structure against an excessive deformation in order to prevent a tearing of the structure.

In particular, the first support structure of the first housing member supports the hydrophobic structure in case a reverse suction force on the hydrophobic structure towards the inlet port arises. If such a suction force arises, the hydrophobic structure may come into abutment with the first support structure, such that an excessive deformation of the hydrophobic structure is prevented.

The second support structure of the second housing member in turn serves to prevent an excessive deformation of the hydrophobic structure towards the outlet opening during normal operation of the filter. In particular, in the presence of a sucking force towards the outlet port the hydrophobic structure may come into abutment with the second support structure such that an excessive deformation of the hydrophobic structure towards the outlet opening is prevented.

In another aspect, in addition or alternatively to the second support structure, at least one support member may extend across the outlet opening. The at least one support member may for example have the shape of a beam extending across the outlet opening (which is formed by a channel for guiding air out of the outlet chamber) in parallel to the plane of extension of the hydrophobic structure. For example, in one embodiment a multiplicity of support members in the shape of beams may extend across the outlet opening and may cross each other such that a cross structure is formed across the outlet opening. In this way an excessive deformation of the hydrophobic structure at the location of the outlet opening can be prevented, the hydrophobic structure being supported at the location of the outlet opening by the one or the multiple support members. By means of the at least one support member additional support for the hydrophobic structure at the location of the outlet opening is provided, hence reducing the risk of a tearing of the hydrophobic structure at the location of the outlet opening.

The provision of at least one support member extending across the outlet opening may represent an inventive concept which may be used by itself.

In particular, a hydrophobic filter for filtering an airflow or another gaseous flow in a medical application may comprise: a housing encompassing a filter chamber, an inlet port arranged on the housing and forming an inlet opening, an outlet port arranged on the housing and forming an outlet opening, and a hydrophobic structure extending along a plane of extension and separating the filter chamber into an inlet chamber and an outlet chamber, wherein the inlet opening opens into the inlet chamber and the outlet opening opens into the outlet chamber. Herein, the filter comprises at least one support member extending across the outlet opening.

The foregoing filter may be suitably combined with a portion or all of the features as described above.

The outlet opening may, in one embodiment, be tapered in a direction towards the hydrophobic structure. Generally, the housing members forming the housing of the filter may be formed from a suitable plastic material, for example as rigid parts using a molding technique, for example an injection molding technique. Herein, to enable the fabrication of the at least one support member at the location at which the outlet opening of the second housing member opens into the outlet chamber, it may be provided that the outlet opening (forming a channel to guide flow out of the outlet chamber) comprises a conicity such that during fabrication of the second housing member a molding tool may be removed from the second housing member in a direction facing away from the side of the second housing member at which the hydrophobic structure is to be arranged when assembling the filter. This allows to form the at least one support member across the outlet opening by injection molding when fabricating the second housing member. The reverse conicity enables the injection molding of the second housing member including the forming of the at least one support member across the outlet opening.

A hydrophobic filter as described above may for example be used in an autotransfusion system for collecting blood from a surgical site of a patient for processing the blood for re-infusion. However, the hydrophobic filter may also be used in another medical application in which air or another gas stream shall be filtered.

The filtering media may, in one embodiment, include a sheet-like, porous fabric made for example in the shape of a membrane or any other porous structure, made from a single layer or from a stack of multiple layers of the same material or different materials. The hydrophobic structure may be fabricated from any suited material known in the art. Hydrophobic filter fabrics may for example be made from a PTFE material, wherein however also other materials are conceivable.

Hydrophobicity in the context of this text is to be understood as the tendency of the filtering media to adsorb little or no water. Whereas a hydrophilic filtering media exhibits an affinity for water and readily adsorbs water, a hydrophobic filtering material has the opposite response to water interaction compared to hydrophilic materials. Hydrophobic materials have little or no tendency to adsorb water and water tends to bead on their surfaces (i.e. to form discrete droplets). Hydrophobic materials generally possess low surface tension values and lack active groups in their surface chemistry for formation of "hydrogen-bonds" with water. Water or other aqueous solutions hence generally may not pass the hydrophobic structure of the filtering media, such that water or other aqueous solutions and also debris particles or the like are blocked by the filter such that air or another gaseous flow is filtered.

The idea underlying the invention shall subsequently be described in more detail with reference to the embodiments shown in the figures. Herein:

FIG. 7 shows a schematic view of a molding tool for forming the second housing member of the hydrophobic filter;

FIG. 8 shows a schematic view of another embodiment of a hydrophobic filter;

FIG. 9 shows a cross-sectional view of the filter according to FIG. 8;

FIG. 10 shows a schematic, cross-sectional view of another embodiment of a hydrophobic filter;

FIG. 11 shows a schematic view of another embodiment of a hydrophobic filter;

FIG. 12 shows a schematic view of yet another embodiment of a hydrophobic filter;

FIG. 13 shows a hydrophobic filter as known in the art; and

FIG. 14 shows a cross-sectional view of the filter according to FIG. 13.

FIG. 1 shows a schematic view of an autotransfusion system 5 which is constituted to draw blood L from a reservoir 2 in order to process the blood for re-infusion into a patient for example during a surgery.

Figure 1:
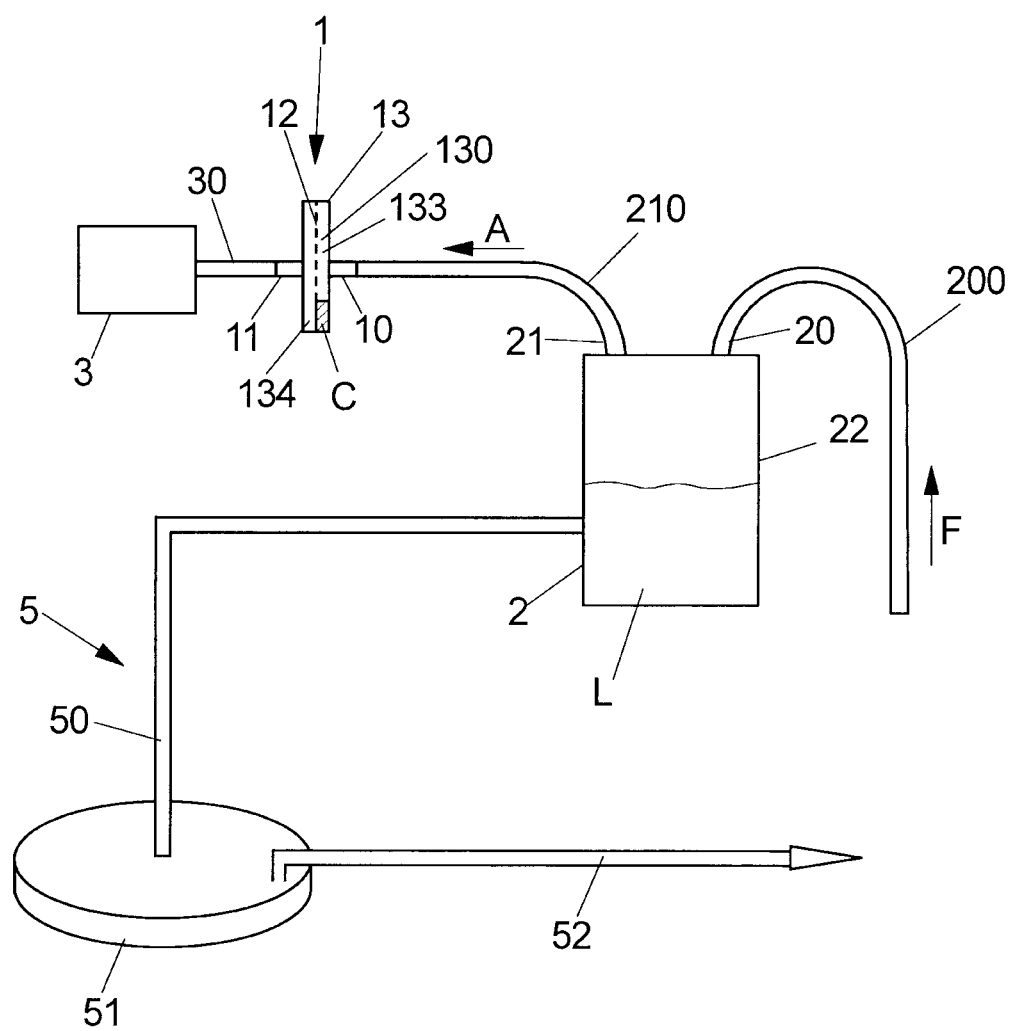
FIG. 1 shows a schematic drawing of an autotransfusion system.

Within the embodiment of FIG. 1, blood L may for example be drawn from a surgical site of a patient via a line 200 into the reservoir 2. By means of a line 50, the blood L collected in the reservoir 2 may be continuously drawn into a separation and washing chamber 51 in which unwanted constituents are removed from the blood L to obtain a packed concentration of red blood cells for re-infusion into the patient via a line 52. The transfusion may take place continuously such that blood L continuously may be collected from the patient and may be continuously processed for re-infusing processed blood components into the patient.

The line 200 is connected to an inlet 20 arranged on a housing 22 of the reservoir 2. A liquid flow F is drawn into the reservoir 2 by creating a negative pressure within the housing 22 of the reservoir 2 in that an airflow A or another gaseous flow (subsequently jointly referred to as airflow) is drawn from the housing 22 by means of a line 210 connected to a port 21 of the housing 22. The airflow A is caused by a negative pressure pump 3, for example constituted as a vacuum pump, which draws air from the housing 22 through the line 210, through a filter 1 connected to the line 210 and through a line 30 extending in between the filter 1 and the pump 3.

The pump 3 serves to draw air from the housing 22. In order to prevent liquid or debris to be drawn towards the pump 3 together with the airflow A, the filter 1 is constituted as a hydrophobic filter having a filtering media including a hydrophobic structure in the shape of a hydrophobic membrane 12 (subsequently in short: hydrophobic membrane) separating a filter chamber 130 into an inlet chamber 133 and an outlet chamber 134. An inlet port 10 is arranged on a housing 13 of the filter 1 and opens into the inlet chamber 133, whereas an outlet port 11 arranged on the housing 13 exits from the outlet chamber 134. The line 210 is in fluid connection with the inlet port 10, whereas the line 30 extending towards the pump 3 is in fluid connection with the outlet port 11.

During operation, and airflow A is continuously drawn through the filter 1. Herein, condensation liquid C may occur within the inlet chamber 133, due to condensation appearing in the inlet chamber 133 as well as due to liquid and debris drawn towards the filter 1 via the line 210 together with the airflow A. Due to the hydrophobicity of the membrane 12, however, liquid and debris may not pass the liquid 12, but remains in the inlet chamber 133. Only air is drawn through the membrane 12 and hence is filtered such that no liquid or debris may flow towards the pump 3.

As shown in FIGS. 13 and 14, a conventional filter 1 may have a round shape (FIG. 13), the inlet port 10 and the outlet port 11 being aligned with each other at a central location with respect to a plane of extension E along which the hydrophobic membrane 12 extends. If condensation liquid C accumulates in the inlet chamber 133 and eventually reaches the location at which the inlet port 10 opens into the inlet chamber 133, the condensation liquid C may hinder air from flowing through the membrane 12 and may act as a plug preventing an efficient filtration operation. This may pose a problem during a surgical operation, in particular if the surgical operation lasts for a prolonged duration (e.g. multiple hours) and an autotransfusion system is to be used continuously during the operation.

There hence is a desire to prevent condensation liquid C from hindering filtration operation and from blocking a substantial portion of the hydrophobic membrane 12, which otherwise may have an effect on the filtration performance.

In an embodiment of a hydrophobic filter 1 shown in FIGS. 2 to 6, the housing 13 of the filter 1 is formed from two housing members 14, 15 connected to each other along a connecting structure 140, 150 circumferentially extending about each housing member 14, 15. The housing members 14, 15 may for example be fixed to each other by gluing or welding. Radially inside the connecting structure 140, 115, each housing member 14, 15 comprises a clamping section 141, 151 circumferentially extending about the housing member 14, 15, the clamping sections 141, 151 being constituted to receive the hydrophobic membrane 12 in between such that the hydrophobic membrane 12 is held in a clamping fashion in between the housing members 14, 15 when the housing members 14, 15 are assembled to form the filter 1. In the assembled state, the hydrophobic membrane 12 separates a filter chamber 130 inside the housing 13 into an inlet chamber 133 and an outlet chamber 134.

An inlet port 10 is arranged on an inlet structure 144 adjoining a tapering structure 143 of the housing member 14. The inlet port 10 forms an inlet opening 100 in the shape of a channel opening into the inlet chamber 133 such that an airflow A may enter through the inlet port 10 into the inlet chamber 133 and may flow towards the hydrophobic membrane 12. As visible from FIG. 2, the tapering structure 143 has a pyramid shape being tapered in a direction away from the hydrophobic membrane 12. The inlet structure 144 adjoining the tapering structure 143 comprises a guide face 144A having a curved shape, the inlet port 10 being arranged on a planar face 144B arranged at an angle of about 90° with respect to the guide face 144A, such that the inlet opening 100 extends along a vertical direction V (see FIG. 4) in parallel to the plane of extension E of the hydrophobic membrane 12, the airflow A hence being guided in the vertical direction V through the inlet opening 100 into the inlet chamber 133 and being guided towards the hydrophobic membrane 12 by means of the curved guide face 144A.

The outlet port 11 on the housing member 15 is arranged at a central location with respect to the hydrophobic membrane 12 and forms an outlet opening 100 in the shape of a channel extending along a horizontal direction H perpendicular to the plane of extension E of the hydrophobic membrane 12. Air which has passed the hydrophobic membrane 12 hence is guided out of the outlet chamber 134 through the outlet opening 110 along the horizontal direction H towards the pump 3 connected to the outlet port 11 by means of the line 30, as schematically shown in FIG. 1.

Figure 4:
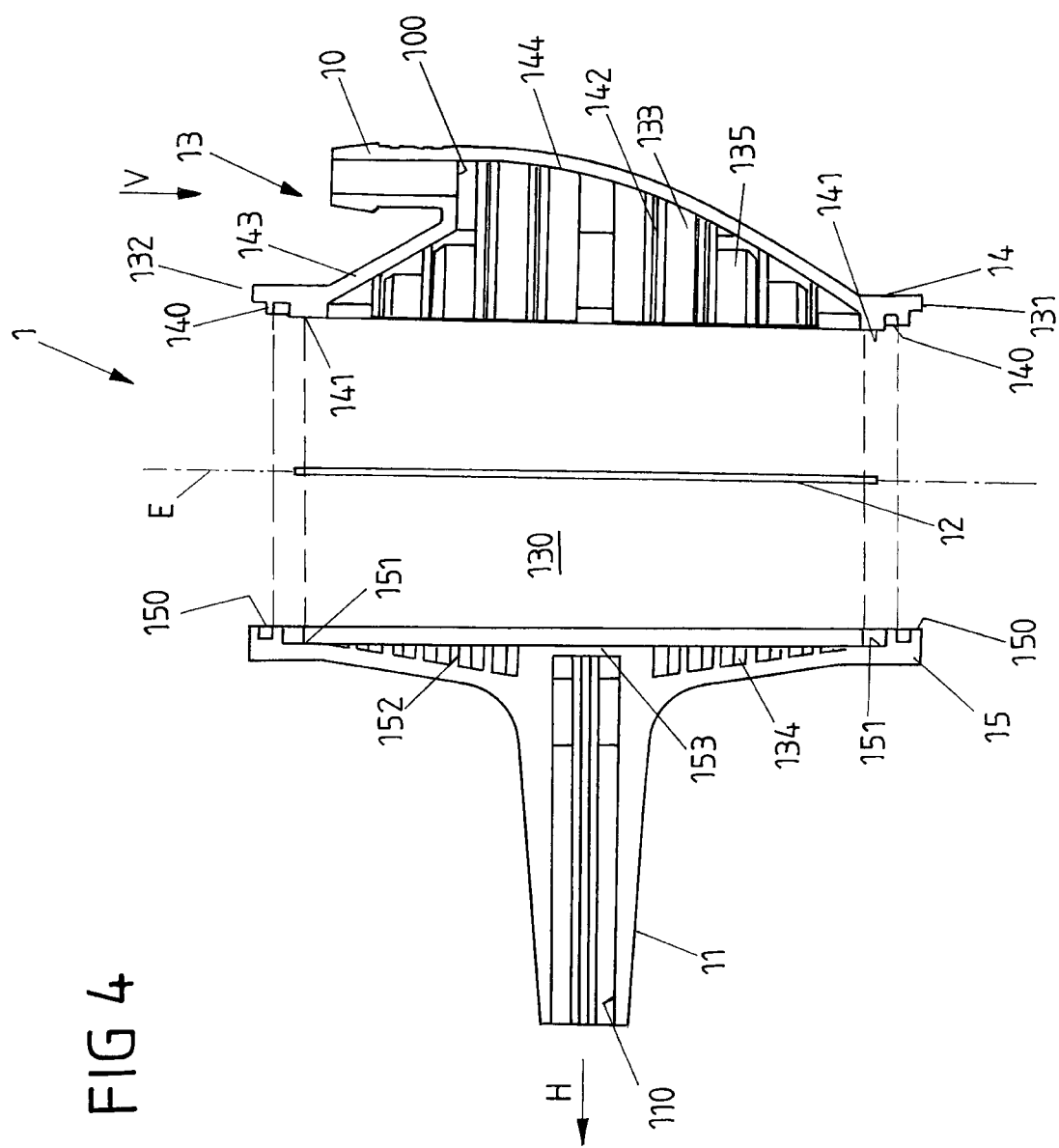
FIG. 4 shows a cross-sectional view of housing members of the hydrophobic filter.

As visible in FIG. 4, the inlet opening 100 enters into the inlet chamber 133 at a location displaced with respect to the outlet opening 110 towards the top 132 of the filter 1. Herein it is to be noted that the filter 1 is to be arranged in a defined position on the autotransfusion system 5, such that the hydrophobic membrane 12 is arranged vertically and the bottom 131 of the housing 13 comes to rest at a lower position with respect to the top 132 of the housing 13.

Because the inlet opening 100 extends along the vertical direction V, air is guided in a beneficial manner into the inlet chamber 133 such that condensation liquid C is collected at the bottom 131 within the inlet chamber 133. Due to the tapering structure 133 a collection chamber 135 is formed having a substantial volume in the region of the bottom 131 within the inlet chamber 133, such that a substantial amount of condensation liquid C may be collected within the inlet chamber 133 without the condensation liquid C blocking an excessive portion of the hydrophobic membrane 12 and without the condensation liquid C accumulating to reach the inlet opening 100. Hence, despite the accumulation of condensation liquid C within the inlet chamber 133, the filter 1 may remain functional over a prolonged duration of use during a surgery.

In addition, because the inlet opening 100 extends along the vertical direction V, the line 210 may be laid to approach the filter 1 along the vertical direction V, such that the line 210 may extend towards the filter 1 in a space-efficient manner.

Furthermore, the filter 1 may be tightly packed in a packaging, because the inlet port 10 does not significantly protrude from the housing 13 of the filter 1.

Figure 2:
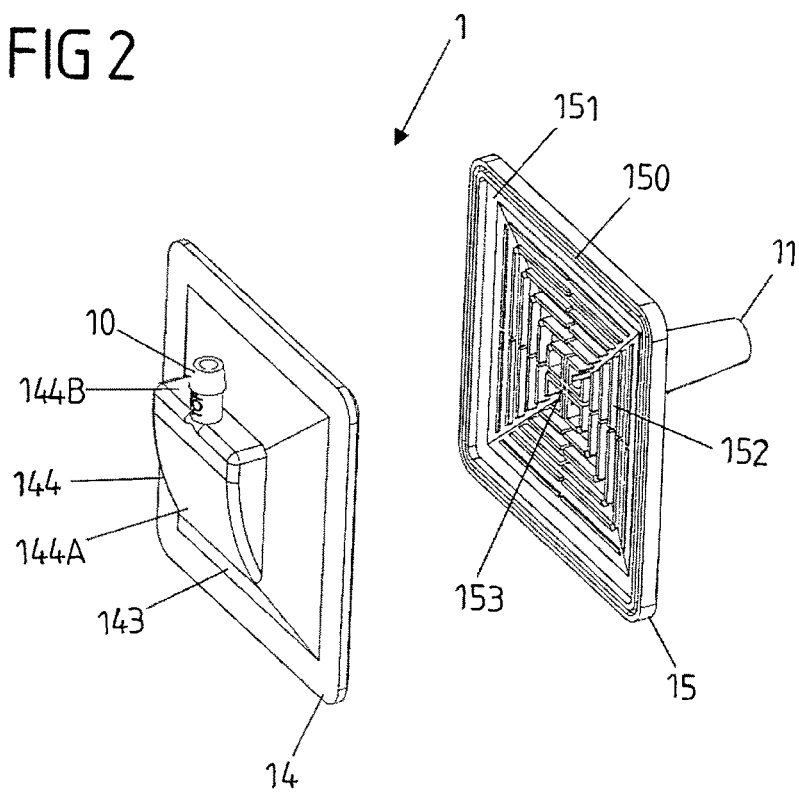
FIG. 2 shows a view of a first embodiment of a hydrophobic filter.
Figure 3:
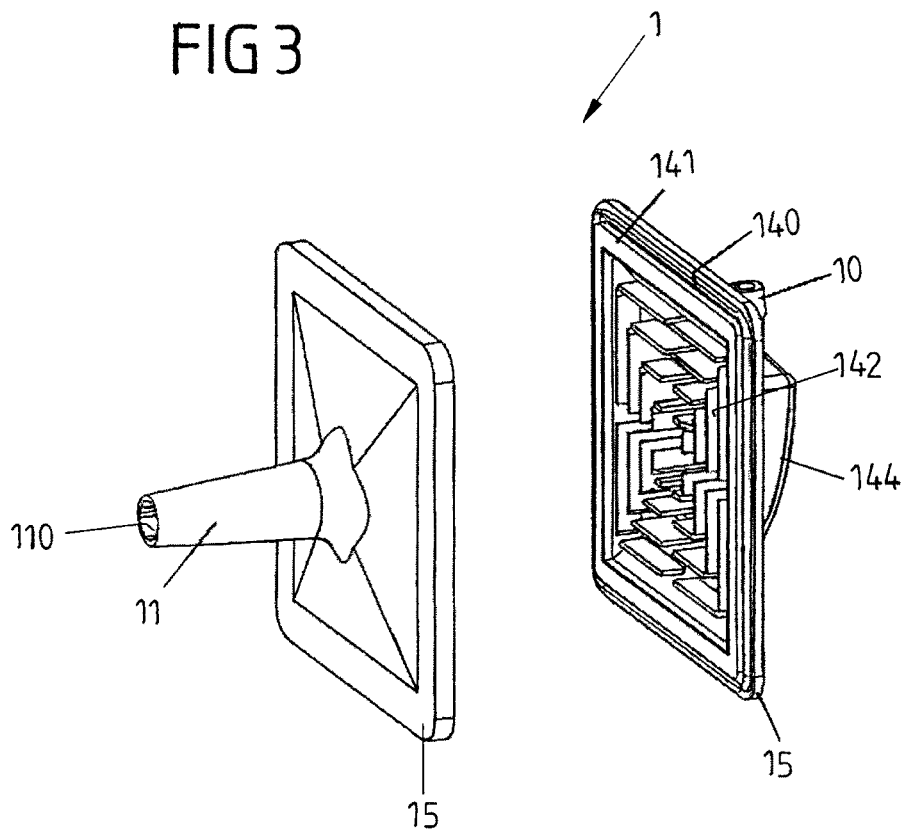
FIG. 3 shows another view of the embodiment of the hydrophobic filter.
Figure 5:
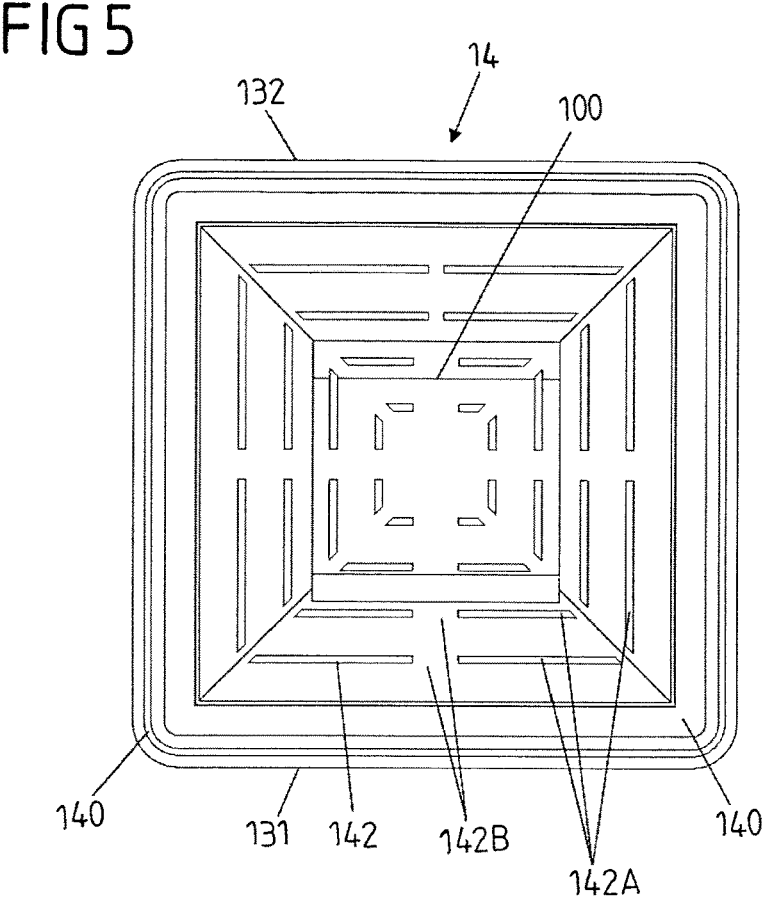
FIG. 5 shows a view into a first housing member of the hydrophobic filter.
Figure 6:
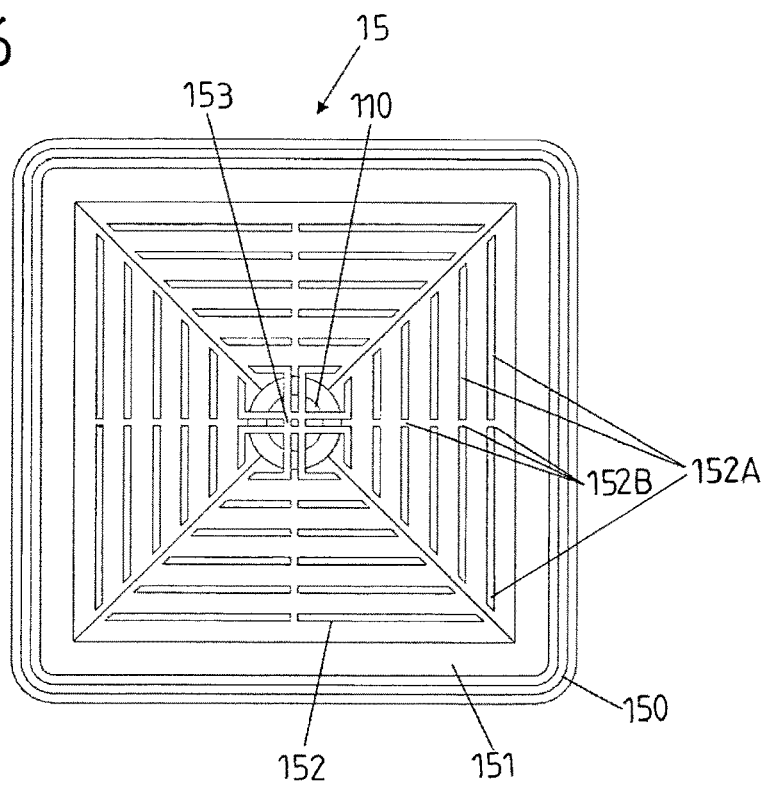
FIG. 6 shows a view into a second housing member of the hydrophobic filter.

As visible from FIGS. 2 and 3 in connection with FIGS. 5 and 6, both on the housing member 14 forming the inlet side of the filter 1 and the housing member 15 forming the outlet side of the filter 1 a support structure 142, 152 is arranged, each support structure 142, 152 being formed by a multiplicity of ridges extending transversely with respect to the plane of extension E of the hydrophobic membrane 12. In particular, the ridges 142A, 152A are arranged to form an arrangement of interleaved squares, wherein neighboring ridges 142A, 152A are separated from each other by gaps 142B, 152B such that air may flow parallel to the plane of extension E through the gaps 142B, 152B separating the ridges 142A, 152A.

The support structures 142, 152 serve to support the hydrophobic membrane 12 against an excessive deformation. During normal operation the hydrophobic membrane 12 experiences a suction force towards the outlet opening 110, the support structure 152 on the housing member 15 forming a support for the hydrophobic membrane 12. In case a reverse pressure arises leading to a suction force towards the inlet opening 100, in turn the hydrophobic membrane 12 may come into abutment with the support structure 142 of the housing member 14, such that in each case an excessive deformation (which otherwise may lead to a tearing of the hydrophobic membrane 12) is prevented.

As visible from FIG. 2 and FIG. 6, support members 153 in the shape of beams extend across the outlet opening 110 and form a cross structure in front of the outlet opening 110. The support members 153 extend in parallel to the plane of extension E and provide for a support for the membrane 12 at the location of the outlet opening 110, preventing the hydrophobic membrane 12 from being drawn into the outlet opening 12 such that the risk of the membrane 12 tearing at the location of the outlet opening 110 is significantly reduced.

Because of the support structures 142, 152 and in addition because of the cross-shaped support members 153 at the location of the outlet opening 110, additional measures to strengthen the hydrophobic membrane 12 may be dispensable. In particular, a reinforcing layer on the hydrophobic membrane 12 to strengthen the hydrophobic membrane 12 may not be necessary, rendering the hydrophobic membrane 12 less expensive.

The housing members 14, 15 beneficially are formed as rigid plastic parts for example by injection molding. Herein, to allow the support members 153 to be formed at the location at which the outlet opening 110 opens into the outlet chamber 134, the outlet opening 110 (having the shape of a channel) may be tapered towards the hydrophobic membrane 12. For example, the outlet opening 110 may have a (slight) conicity with a narrow end 110B and a wider end 110A (see FIG. 7). This allows forming the housing member 15 using a molding tool 4 comprising a recess 40 for forming the housing member 15 and a pin 41 for forming the outlet opening 110 within the outlet port 11. Because of the tapered shape of the outlet opening 110, the pin 41 may be removed in a pulling direction P from the outlet opening 110 formed within the housing member 15, such that the support members 153 may be formed in a single molding step together with other portions of the housing member 15 using the molding tool 4.

As visible from FIGS. 2 and 3, the filter 1 has a square shape when viewed along the plane of extension E of the hydrophobic membrane 12. This additionally causes the inlet chamber 133 to have a substantial volume close to the bottom 131 of the housing 13 such that a substantial amount of condensation liquid C may be collected within the inlet chamber 133 without hindering the filtration process.

In another embodiment shown in FIGS. 8 and 9, the inlet port 10 is placed close to the top 132 of the filter 1, such that condensation liquid C may accumulate within the inlet chamber 133 without reaching the location at which the inlet port 10 opens into the inlet chamber 133.

In a modified embodiment shown in FIG. 10, the volume of the inlet chamber 133 in the region of the bottom 131 of the housing 13 is increased to form a collection chamber 135 in the region of the bottom 131. For this, the inlet chamber 133, when viewed in cross-section perpendicular to the plane of extension E of the hydrophobic membrane 12, widens towards the bottom 131, the inlet chamber 133 having a polygonal shape as visible from FIG. 10. Due to a wide chamber volume being provided close to the bottom 131 within the inlet chamber 133, condensation liquid C may accumulate within the inlet chamber 133 without blocking a substantial portion of the hydrophobic membrane 12.

In another embodiment shown in FIG. 11, a collection chamber 135 may be formed on the inlet chamber 133 extending beneath a lower, bottom edge of the hydrophobic membrane 12. Hence, condensation liquid C may accumulate within the collection chamber 135 without even reaching the hydrophobic membrane 12, such that condensation liquid C does not at all block the hydrophobic membrane 12 and hence does not impact the filtration performance. The collection chamber 135 may have any desired shape and may be designed such that an amount of condensation liquid C which reasonably can be expected over a prolonged duration of use of the filter 1 can be reliably collected within the collection chamber 135.

In an embodiment shown in FIG. 12 an additional drainage port 16 is formed on the inlet chamber 133 close to the bottom 131 of the housing 13. Through the drainage port 16 condensation liquid C may be drained (draining flow D) such that a substantial accumulation of condensation liquid C within the inlet chamber 133 can be prevented.

The idea of the invention is not limited to the embodiments described above, but may be implemented in an entirely different fashion in completely different embodiments.

A filter as described herein may be used on an autotransfusion system, but may be used also in other medical applications for filtering a gas flow, for example in a respirator.

The filter may be used together with a vacuum pump or any other type of pump causing a negative pressure such that a gas flow is drawn through the filter.

The hydrophobic structure may be made from any suitable material and is constituted to prevent a liquid flow through the hydrophobic structure, but allows a gas flow, in particular an airflow, to pass.

The hydrophobic structure may extend, in a sheet-like fashion, in the filter along a flat plane of extension. It however is also conceivable that the plane of extension is curved in space.

LIST OF REFERENCE NUMERALS

1 Filter
10 Inlet port
100 Inlet opening
11 Outlet port
110 Outlet opening
110A, 110B End
12 Hydrophobic membrane
13 Housing
130 Filter chamber
131 Bottom
132 Top
133 Inlet chamber
134 Outlet chamber
135 Collection chamber
14 Housing member
140 Connecting structure
141 Clamping section
142 Support structure
142A Ridges
142B Gaps
143 Tapering structure
144 Inlet structure
144A Guide face
144B Planar face
15 Housing member
150 Connecting structure
151 Clamping section
152 Support structure
152A Ridges
152B Gaps
153 Support member (cross structure)
16 Drainage port 2 Reservoir
20 Inlet
200 Line
21 Vacuum port
210 Line
22 Housing
3 Suction pump (vacuum pump)
30 Line
4 Molding tool
40 Recess
41 Pin
5 Autotransfusion system
50 Line
51 Separating and washing chamber
52 Line
A Airflow or another gaseous flow
C Condensation liquid
D Drainage flow
E Plane of extension
F Liquid flow
L Liquid
H Horizontal direction
V Vertical direction

The invention claimed is:

1. A hydrophobic filter for filtering an airflow or another gaseous flow in a medical application, the filter comprising:
   a housing comprising a bottom and a top and encompassing a filter chamber;
   an inlet port arranged on the housing and forming an inlet opening;
   an outlet port arranged on the housing and forming an outlet opening; and
   a filtering media comprising a hydrophobic structure extending from the top of the housing toward the bottom of the housing and separating the filter chamber into an inlet chamber and an outlet chamber, wherein the outlet opening opens into the outlet chamber at a first location and the inlet opening opens into the inlet chamber at a second location displaced with respect to the first location towards the top of the housing.

2. The hydrophobic filter of claim 1, wherein the inlet chamber forms a collection chamber for collecting condensation liquid at the bottom of the housing.

3. The hydrophobic filter of claim 2, wherein the inlet chamber widens towards the bottom of the housing to form the collection chamber in the vicinity of the bottom of the housing.

4. The hydrophobic filter of claim 3, wherein the collection chamber is displaced with respect to the first location towards the bottom of the housing.

5. The hydrophobic filter of claim 3, wherein the hydrophobic structure extends from the top of the housing to the bottom of the housing.

6. The hydrophobic filter of claim 3, wherein
   the inlet port is associated with a wall of the housing extending generally parallel to a plane defined by the hydrophobic structure, and
   a portion of the collection chamber is positioned between said wall and the bottom of the housing.

7. The hydrophobic filter of claim 3, wherein
   the inlet port is associated with a wall of the housing extending generally parallel to a plane defined by the hydrophobic structure, and
   a portion of the collection chamber extends in a direction away from the hydrophobic structure beyond said wall.

8. The hydrophobic filter of claim 3, wherein
   the inlet port is associated with a wall of the housing extending generally parallel to a plane defined by the hydrophobic structure,
   a portion of the bottom of the housing extends generally perpendicular to said wall, and
   a portion of the collection chamber is defined by a second wall extending at an angle from said wall to said portion of the bottom of the housing.

9. The hydrophobic filter of claim 2, wherein the collection chamber extends beneath a bottom edge of the hydrophobic structure.

10. The hydrophobic filter of claim 1, wherein the inlet chamber comprises a drainage port for draining condensation liquid from the inlet chamber.

11. The hydrophobic filter of claim 10, wherein
   the inlet chamber forms a collection chamber for collecting condensation liquid at the bottom of the housing, and
   the drainage port is associated with the collection chamber.

12. The hydrophobic filter of claim 11, wherein the hydrophobic structure extends from the top of the housing to the bottom of the housing.

13. The hydrophobic filter of claim 10, wherein the drainage port is displaced with respect to the first location towards the bottom of the housing.

14. The hydrophobic filter of claim 1, wherein
   the outlet opening extends along a horizontal direction for guiding the airflow or another gaseous flow out of the filter chamber along the horizontal direction, and
   the inlet opening extends along the horizontal direction for guiding the airflow or another gaseous flow into the filter chamber along the horizontal direction.

15. The hydrophobic filter of claim 1, wherein the outlet port is arranged at a central location with respect to the hydrophobic structure.

16. The hydrophobic filter of claim 1, wherein the outlet port and the outlet opening are substantially parallel to the inlet port and the inlet opening.

17. The hydrophobic filter of claim 1, wherein the filter chamber has a generally square or rectangular cross-sectional configuration parallel to a plane defined by the hydrophobic structure.

18. The hydrophobic filter of claim 1, wherein the inlet opening is positioned directly adjacent to the top of the housing.

19. The hydrophobic filter of claim 1, wherein
   the housing comprises a first housing member on which the inlet port is formed and a second housing member on which the outlet port is formed,
   the first housing member comprises a first clamping section and the second housing member comprises a second clamping section, and
   the hydrophobic structure is clamped in between the first clamping section and the second clamping section.

20. The hydrophobic filter of claim 19, wherein
   the first housing member comprises a first support structure formed by a multiplicity of ridges for supporting the hydrophobic structure against a deformation towards the inlet opening, and
   the second housing member comprises a second support structure formed by a multiplicity of ridges for supporting the hydrophobic structure against a deformation towards the outlet opening.

* * * * *